(12) United States Patent
Lemer

(10) Patent No.: US 12,364,448 B2
(45) Date of Patent: Jul. 22, 2025

(54) SCREEN FOR PROTECTION AGAINST IONIZING RADIATION EMISSIONS

(71) Applicant: LEMER PAX, La Chapelle sur Erdre (FR)

(72) Inventor: Pierre-Marie Lemer, Nantes (FR)

(73) Assignee: LEMER PAX, La Chapelle sur Erdre (FR)

( * ) Notice: Subject to any disclaimer, the term of this patent is extended or adjusted under 35 U.S.C. 154(b) by 535 days.

(21) Appl. No.: 17/793,346

(22) PCT Filed: Jan. 13, 2021

(86) PCT No.: PCT/EP2021/050531
§ 371 (c)(1),
(2) Date: Jul. 15, 2022

(87) PCT Pub. No.: WO2021/144289
PCT Pub. Date: Jul. 22, 2021

(65) Prior Publication Data
US 2023/0058574 A1 Feb. 23, 2023

(30) Foreign Application Priority Data

Jan. 16, 2020 (FR) ..................................... 2000403

(51) Int. Cl.
*A61B 6/10* (2006.01)
(52) U.S. Cl.
CPC .................................... *A61B 6/107* (2013.01)
(58) Field of Classification Search
USPC ...................................................... 250/515.1
See application file for complete search history.

(56) References Cited

U.S. PATENT DOCUMENTS

| 3,308,297 A | 3/1967 | Mansker |
| 2005/0173658 A1* | 8/2005 | Lemer ............... A61B 6/107 250/515.1 |

(Continued)

FOREIGN PATENT DOCUMENTS

| FR | 2 915 868 | 11/2008 |
| JP | S6368305 U | 5/1988 |

(Continued)

OTHER PUBLICATIONS

International Search Report for PCT/EP2021/050531 dated Apr. 1, 2021, 4 pages.

(Continued)

*Primary Examiner* — Kiet T Nguyen
(74) *Attorney, Agent, or Firm* — NIXON & VANDERHYE

(57) ABSTRACT

Disclosed is a radiation protection screen for protecting an operator against emissions of ionizing radiation of the X-ray type or other types. This radiation protection screen includes a front wall provided with a transparent panel and with an airlock structure adapted to the passage of equipment and/or the arms of the operator. The airlock structure includes an airlock opening associated with a flexible closing structure, which airlock opening includes a horizontal or approximately horizontal lower opening edge. And the screen further includes a support device suitable for supporting material and/or an arm of the operator, which support device is arranged at the level of the lower opening edge of the airlock structure, on the side of the inner face of the front wall.

20 Claims, 4 Drawing Sheets

(56) References Cited

U.S. PATENT DOCUMENTS

| | | |
|---|---|---|
| 2006/0076522 A1 | 4/2006 | Goldstein |
| 2010/0304060 A1 | 12/2010 | Lemer |
| 2012/0049093 A1 | 3/2012 | Costea |
| 2015/0335297 A1* | 11/2015 | Mogul ............... G21F 3/00 250/515.1 |
| 2020/0100736 A1 | 4/2020 | Lemer |

FOREIGN PATENT DOCUMENTS

| | | |
|---|---|---|
| JP | 2010525910 A | 7/2010 |
| JP | 2012042292 A | 3/2012 |
| WO | 2009/156660 | 12/2009 |
| WO | 2018/109380 | 6/2018 |

OTHER PUBLICATIONS

Written Opinion of the ISA for PCT/EP2021/050531 dated Apr. 1, 2021, 5 pages.

* cited by examiner

SCREEN FOR PROTECTION AGAINST IONIZING RADIATION EMISSIONS

CROSS-REFERENCE TO RELATED APPLICATIONS

This application is the U.S. national phase of International Application No. PCT/EP2021/050531 filed Jan. 13, 2021 which designated the U.S. and claims priority to FR 2000403 filed Jan. 16, 2020, the entire contents of each of which are hereby incorporated by reference.

BACKGROUND OF THE INVENTION

Field of the Invention

The present invention generally relates to the field of equipment for protection against ionizing radiation.

It relates more particularly to radio-protective screens which are used in a medical or other environment, to protect an operator against emissions of ionizing radiation, for example X-rays. It also relates to equipment in the form of a cover for the dressing by covering such screens, for their use in a sterile protected environment.

Description of the Related Art

In the context of certain examinations or interventions, patients are exposed to ionizing radiation, in particular of the X-ray type, which are used for the purpose of control, diagnosis or treatment.

This is particularly the case for interventions such as catheterization, fitting of pacemakers, vascular, neurological or urological examinations, CRM (Cardiac Rhythm Management), CRT (Cardiac Resynchronization Therapy) or when implementing fluoroscopy techniques.

In particular, fluoroscopy is an imaging technique that consists in using X-rays to obtain real-time images of an object.

In the medical field, its application allows the visualization of the structures and functions of the internal organs of a patient, such as, for example, the heartbeat or the passage of blood in the blood vessels. This technique is used for diagnosis as well as therapy; and it is used in the interventional fields, in particular radiology, cardiology, neurology, electrophysiology, peripheral vascular radiology, interventional pediatrics, etc.

The rooms dedicated to these specialties are equipped with fluoroscopy devices (also called C-arms) which take the general form of a mobile technical box extending by a large arch, one end of which includes an X-ray emitting device and the other end of which is equipped with a detector.

In equipped rooms, catheters and probes are introduced through an access route (generally the femoral or radial artery) for diagnostic or therapeutic purposes. The vascular network is visualized through the use of X-rays, often coupled with an injection of contrast product(s).

These fluoroscopy devices occupy an important space around the examination table and their positioning is frequently modified according to the area of the patient's body to be inspected or treated.

Certain types of interventions require the assistance of echography techniques, in particular to visualize the parts of the heart which are transparent to X-rays, therefore not visible on fluoroscopy screens.

This technology using ultrasound is, for example, implemented for placing staple(s) on the mitral valve when the latter does not close sufficiently well and is no longer sufficiently sealed.

Such transesophageal echography techniques allow visualization of the intracardiac cavity and in detail the morphology and abnormalities of the left atrium and posterior ventricle wall. They use a tube-shaped probe which is inserted into the pharynx and then into the esophagus, with the transducer facing the right side of the patient's heart. A probe control box is placed upstream of the probe to allow the practitioner to make the various desired settings.

Upstream, the probe control box is connected to a console comprising in particular a screen for displaying the cardiac image.

It will be understood that it is important to properly protect the operators (doctors, surgeons, technicians, nurses or others) against the emitted ionizing radiation, (of the primary type, coming directly from the emitter, or of the secondary type: reflected by the equipment and coming directly from the patient himself), under penalty of exposing them to large doses, accumulated over time, likely to cause various pathologies (necroses of the upper limbs, brain tumors, cataracts, radiodermatitis, and so on).

For this, protective structures exist which consist of clothing such as blouses, chasubles, aprons made of radioprotective material, thyroid protectors, glasses, etc., but which do not always cover the entire body and whose heavy weight is detrimental to the operator's comfort, limits his ability to move and leads to rapid fatigue. In addition, their equivalence of lead protection is 0.5 mm maximum thickness.

There also are screens or shields consisting of panels or assemblies of panels made of suitable radio-protective material, suspended from a suitable support or placed on the ground, either directly or by means of a rolling base.

Such radiation-protective screen structures are described in documents US-2012/0049093, US-2006/0076522, FR-2 915 868, WO-2009/156660, or further US-3 308 297.

However, the screen structures known hitherto are not completely suited to the implementation of the aforementioned echography techniques, in particular due to the presence of materials or equipment which must be handled during such interventions.

SUMMARY OF THE INVENTION

In order to remedy the aforementioned drawback of the state of the art, the present invention proposes a radiation protection screen to ensure the protection of an operator against the emissions of ionizing radiation of the X-ray type or other, which screen comprises a front wall made at least in part of a radio-protective material, which front wall comprises an inner face of the front wall, oriented towards the positioning space of the operator, an outer face of the front wall, opposite to the said inner face of the front wall, an upper part, a lower part and an intermediate part located between said upper and lower parts, which upper part comprises at least one transparent panel and which intermediate part comprises an airlock structure, suitable for the passage of material(s) and/or of arms of said operator, this radiation protection screen being characterized in that said airlock structure comprises an airlock opening associated with a flexible closing structure, which airlock opening comprises a lower horizontal or approximately horizontal opening edge, and in that it comprises a support device suitable for supporting material(s) and/or an operator's arm, which support device is arranged at the level of said lower opening edge, on the side of said inner face of the front wall.

Such a support device which extends into the positioning space of the operator facilitates the manipulation of materials or equipment by this operator, thus reducing his fatigue over time and increasing the precision of his gestures.

Other non-limiting and advantageous characteristic features of the radiation protection screen in accordance with the invention, taken individually or according to all technically possible combinations, are the following ones:

said support device comprises a proximal end located close to said lower edge of the opening and an opposite distal end, and said proximal end of said support device is pivotally mounted around a vertical or approximately vertical axis;

the radiation protection screen comprises adjustment means to allow adjustment of the position of said support device over at least part of the length of said lower opening edge;

said adjustment means consist of a rail structure formed along said lower edge of the opening, cooperating with a slider structure integral with said support device, which slider structure is provided with locking means adapted to allow locking of its position on said rail structure;

said support device is in the form of an elongated body;

said support device is in the form of a chute with a U-section;

said front wall of the radiation protection screen comprises (a) an outer panel, forming at least a part of said outer face of the front wall, which outer panel comprises an outer panel opening located at the level of the intermediate part of the front wall, and (b) an interior panel, movable vertically, arranged facing said exterior panel opening, on the side of said interior face of the front wall, which interior panel comprises an interior panel opening, which interior panel opening comprises said flexible closing structure and comprises said opening lower edge equipped with said support device, which outer panel opening and which inner panel opening together form said airlock opening, and which inner panel is movably mounted vertically relative to said outer panel so as to allow the height level of said airlock opening to be adjusted;

said inner panel is movably mounted along vertical rails provided on said outer panel, in association with weight compensating means, which inner panel is provided with a maneuvering handle and comprises an indexing finger cooperating with a plurality of indexing holes provided on said outer panel, to ensure the locking of its position in height;

said interior panel opening and said exterior panel opening each comprise two opening parts juxtaposed horizontally and separated by a vertical upright;

the flexible closing structure consists of a juxtaposition of a plurality of vertical strips made of radio-protective material;

said front wall extends in a vertical or approximately vertical plane and comprises two side edges, at least one of said side edges of said front wall being extended by a side wall which extends in a vertical or approximately vertical plane, at an angle of between 90° and 140° with respect to the plane of said front wall, seen from the side of said inner face of the front wall, which side wall(s) comprise(s) an outer side edge equipped with a flexible flap made of radio-protective material;

said front wall extends in a vertical or approximately vertical plane and comprises two side edges each extending by a side wall, which side walls each extend in a vertical or approximately vertical plane, at an angle between 90° and 140° relative to the plane of said front wall, seen from the side of said inner face of the front wall, and said airlock structure extends over the full width of said front wall and extends over a portion of the width of each of said side walls;

the radiation protection screen comprises a screen mounted on a screen support fixed to said inner face of the front wall or, where appropriate, to an inner face of one of its side walls;

the radiation protection screen comprises a base provided with ground support wheels, and the lower part of its front wall and, if necessary, a lower part of its side walls comprises a panel of flexible radiation-protective material.

The present invention also relates to an equipment in the form of a cover intended to cover at least part of the height of a radiation protection screen as defined above, comprising:

(a) at least one flexible panel adapted to at least partially cover said front wall and, where appropriate, at least partially said side wall or walls, said at least one flexible panel comprising at least one transparent part intended to be positioned opposite the transparent panel of the upper part of the said front wall, and means for fixing to the said front wall and/or, where applicable, to the said side wall or walls, (b) at least one flexible airlock structure, adapted to at least partially cover the flexible closing structure associated with said airlock opening of said airlock structure, which at least one flexible airlock structure is in the form of a flexible pocket provided with an opening, which flexible pocket is adapted to cover said flexible closing structure by engagement of the lower edge of the latter in said opening of said flexible pocket, which flexible airlock structure is provided with means for its attachment to said airlock structure, and (c) a flexible support device pocket, for covering said support device adapted to support material(s) and/or an operator's arm, which flexible support device pocket comprises a pocket opening for its positioning on said support device, which flexible pocket of support device is provided with means for its attachment to said support device.

Of course, the different characteristic features, variants and embodiments of the invention can be associated with each other in various combinations insofar as they are not incompatible or exclusive of each other.

BRIEF DESCRIPTION OF THE DRAWINGS

In addition, various other characteristic features of the invention emerge from the appended description made with reference to the drawings which illustrate non-limiting forms of embodiment of the invention and where.

DESCRIPTION OF THE PREFERRED EMBODIMENTS

Figure 1:
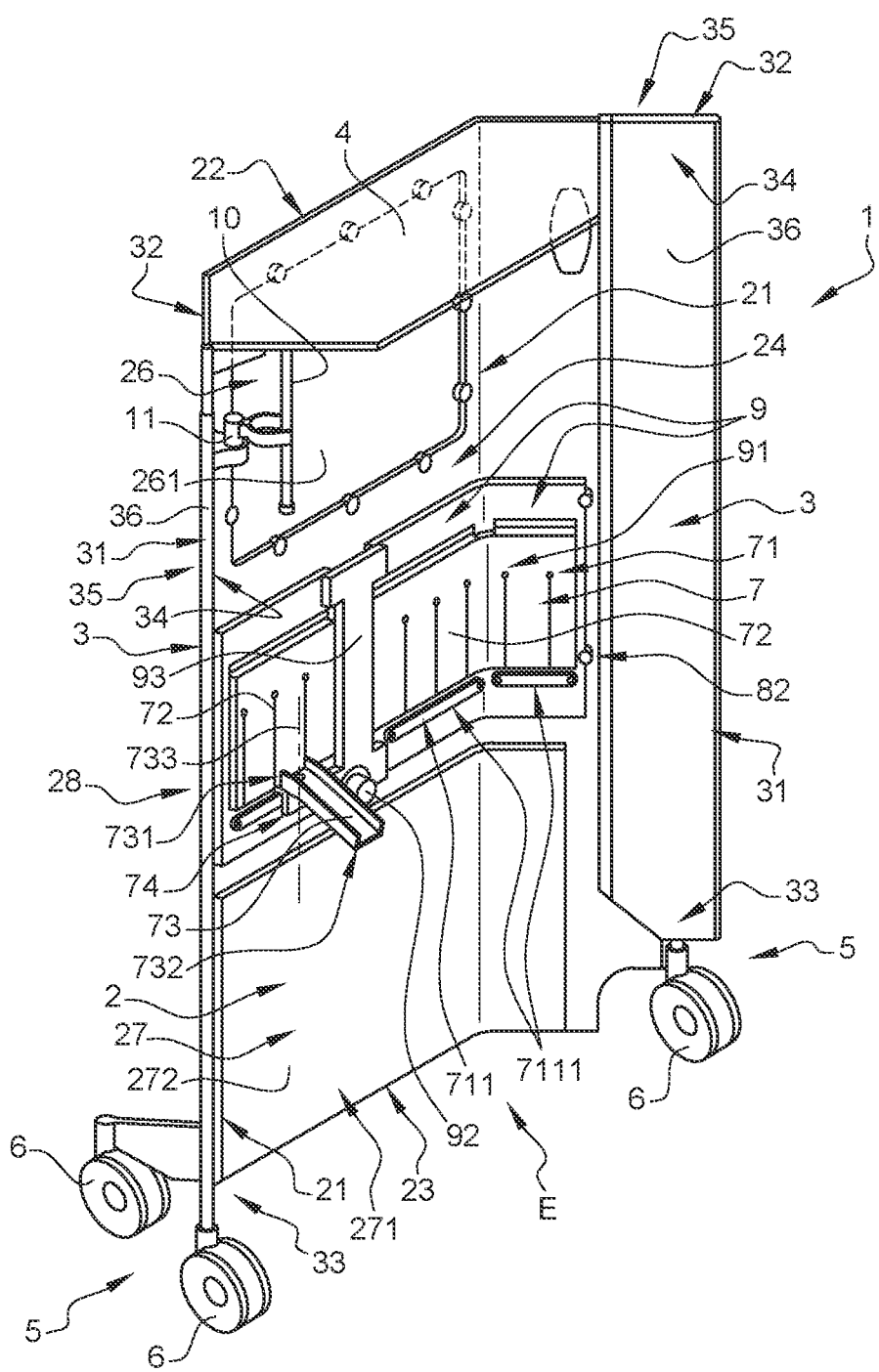
FIG. 1 shows a radio-protective screen according to the invention, seen in perspective from the interior side, that is to say from the side of the operator's positioning space.

The radiation protection screen 1 illustrated in FIGS. 1 to 5 is suitable for protecting an operator against ionizing radiation emitted by a source of ionizing radiation, for example X-rays emitted by a C-arm type fluoroscopy device, in a hospital operating room.

For this, the various component parts of this radio-protective screen 1 are made of radio-protective material(s) having an appropriate lead equivalence, of at least 0.2 mm, depending on the component parts concerned. For example, for all the constituent parts, this lead equivalence is between 0.5 mm and 3 mm.

More particularly, the radiation protection screen 1 consists of a metal framework, for example steel, which is associated with various panels made of suitable radio-protective material, such as transparent panels or flexible panels.

As illustrated in FIGS. 1 to 5, this radio-protective screen 1 is in the form of a mobile cabin comprising a front wall 2 extended on the sides by side walls 3, and in the upper part by a ceiling structure 4, the assembly being mounted on a base 5 provided with wheels 6 for ground support.

The front wall 2 extends in a vertical or approximately vertical plane.

This front wall 2, of generally rectangular shape, is delimited by two side edges 21, an upper edge 22 and a lower edge 23. It comprises an inner face of the front wall 24, oriented towards the operator positioning space E, and a front wall outer face 25, opposite said front wall inner face 24.

Each one of the side walls 3 extends one of the side edges 21 of the front wall 2.

Each side wall 3 is generally rectangular in shape and extends over all, or almost all, of the height of the adjacent side edge 21 of the front wall 2.

Each one of these side walls 3 extends in a vertical or approximately vertical plane, and this in an inclined manner at an angle X (FIG. 5) comprised between 90° and 140° relative to the plane of the front wall 2, seen from the side of the inner face of the front wall 24.

Preferably, this angle X between the inner face of the front wall 24 and each side wall 3 is between 110° and 120°.

In addition, each one of these side walls 3 is delimited by an outer side edge 31, an upper edge 32 and a lower edge 33, and comprises an inner face of the side wall 34, oriented towards the operator positioning space E, as well as a side wall outer face 35, opposite said side wall inner face 34.

The outer side edge 31 of the side walls 3 is fitted with a flexible flap 36 made of radio-protective material. Such flexible side flaps 36 make it possible to absorb shocks and they limit the risks of deterioration of the screen 1 or of surrounding equipment in the event of contact with this equipment.

The flexible flaps 36 consist for example of a sheet of flexible radio-protective material covered with a protective fabric resistant to liquid splashes, this sheet being advantageously folded over on itself to form a double thickness.

The upper part 26 of the front wall 2 comprises a transparent panel 261 to allow the operator to visually access the other side of the screen 1. For example, this transparent panel 261 can be made of lead glass or of plastic material loaded with radio-protective material.

In the illustrated embodiment, the transparent panel 261 extends over part of the width of the front wall 2. In a variant embodiment, this transparent panel 261 can occupy the entire width of the front wall 2; and optionally it can also extend laterally to occupy part of the surface of the side walls 3.

On its part, the lower part 27 of the front wall 2 comprises an opening 271 filled by a panel 272 of flexible radio-protective material. This flexible panel 272 is capable of deforming under contact with equipment (for example the fluoroscopy C-arm), to prevent its degradation, while constituting an effective barrier against ionizing radiation.

Here, this panel 271 of flexible radio-protective material occupies the entire width of the front wall 2 and also part of the surface of the side walls 3. In a variant embodiment, the panel 271 of flexible radio-protective material can extend over only part of the width of the front wall 2.

The flexible panel 272 can for example consist of a multi-sheet assembly of flexible radiation-protective material covered with a protective fabric resistant to liquid splashes, the whole forming a flexible radiation-protective curtain.

Between its upper part 26 and its lower part 27, the front wall 2 comprises an intermediate part 28 provided with an airlock structure 7 allowing the passage of material(s) and/or the arms of the operator on the other side of the screen.

The airlock structure 7 comprises an airlock opening 71 associated with a flexible closing structure 72. The airlock opening 71 comprises a lower opening edge 711 and this lower opening edge 711 comprises a support device 73 which is suitable for supporting material(s) and/or supporting an operator's arm.

The support device 73 is arranged on the side of the inner face of the front wall 24 (that is to say, it extends from the lower edge of the opening 711 in the positioning space E of the operator). Here, it consists of an elongated body in the form of a U-section chute. It comprises a proximal end 731 fixed at the lower edge of the opening 711 and an opposite distal end 732, which extends into the positioning space E. The proximal end 731 of the support device 73 is pivotally mounted close to the lower edge of the opening 711, around an axis 733 that is vertical or approximately vertical.

The position of the support device 73 can be adjusted over at least part of the length of the lower edge of the opening 711.

To this end, the proximal end 731 of the support device 73 comprises a slider structure 74 which is adapted to cooperate with a rail structure 7111 made along the lower edge of the opening 711.

Preferably, the slider structure 74 is provided with locking means 75 adapted to allow locking of its position (and therefore of the position of the support device 73) on the rail structure 7111. These locking means 75 can for example consist of a clamping screw carried by the slider structure 74 and the end of which is arranged to come into contact with the rail structure 7111, or even a piston with spring return.

It is understood that an operator present in the positioning space E can use the support device 73 as an arm or equipment support when he works through the airlock 7. For example, the support device 73 can serve as a support for the box control of the probe of the intracardiac echography equipment manipulated by a sonographer operator, in assistance to the cardiac surgeon.

The positioning of the support device 73 along the rail structure 7111 is adjusted according to the morphology of the sonographer operator. And the pivoting mounting of this support device 73 around the vertical axis 733 facilitates the movements of the operator during his intervention.

The general shape and the structure of the support device 73 can be adapted according to the material/equipment intended to be supported and manipulated by the operator.

More specifically, the front wall 2 of the radio-protective screen 1 comprises:
(a) an outer panel 8, provided with an outer panel opening 81 located at the intermediate front wall portion 28, and
(b) an inner panel 9, movable vertically, arranged facing said outer panel opening 81, on the side of the inner face of the front wall 24, which inner panel 9 comprises an inner panel opening 91 which itself comprises the flexible closing structure 72, as well as the lower edge of the opening 711 equipped with the support device 73.

The outer panel opening 81 and the inner panel opening 91 together form the aforementioned airlock opening 71.

The outer panel opening 81 is larger than the inner panel opening 91 and the airlock opening 71 is defined by the positioning of the inner panel opening 91 opposite the outer panel opening 81. The dimensions and the positioning of the exterior panel opening 81 are adapted to allow all admissible/desired positions in height of the interior panel opening 91.

The inner panel 9 is mounted vertically relative to the outer panel 8 so as to allow the level of height of the inner panel opening 91, and therefore of the airlock opening 71, to be adapted.

To this end, the inner panel 9 is guided by vertical rails 82 provided on the outer panel 8, on the face of the latter oriented towards the positioning space E. This inner panel 9 is further provided with a maneuvering handle 92 and indexing means to ensure the locking of its height position. For example, the indexing means consist of a retractable indexing finger fitted to the maneuvering handle 92, cooperating with a plurality of indexing orifices (not shown) provided on the outer panel 8. The maneuvering handle 92 can then have a possibility of horizontal movement, perpendicular to the movement of the inner panel 9, and be associated with a return means in the locking position.

Preferably the radio-protective screen 1 further comprises weight compensating means, not shown, which make it possible to compensate for the weight of the interior panel 9 of the airlock, in order to facilitate its height position adjustment. These weight compensating means may consist of one or more jacks (for example gas-type jacks), interposed between the outer panel 8 and the inner panel 9.

Figure 2:
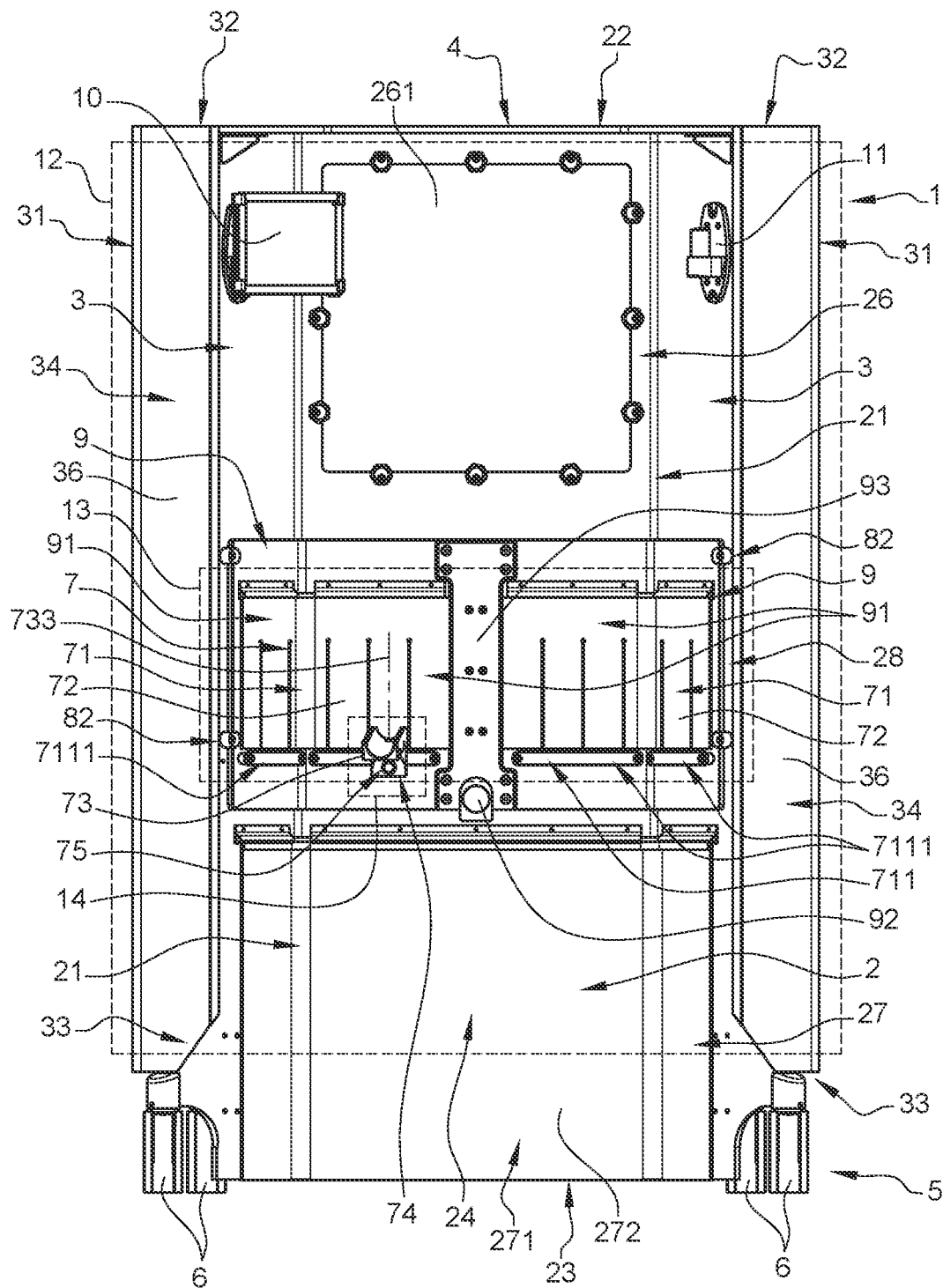
FIG. 2 is a front view of the interior side of the radio-protective screen of FIG. 1.
Figure 3:
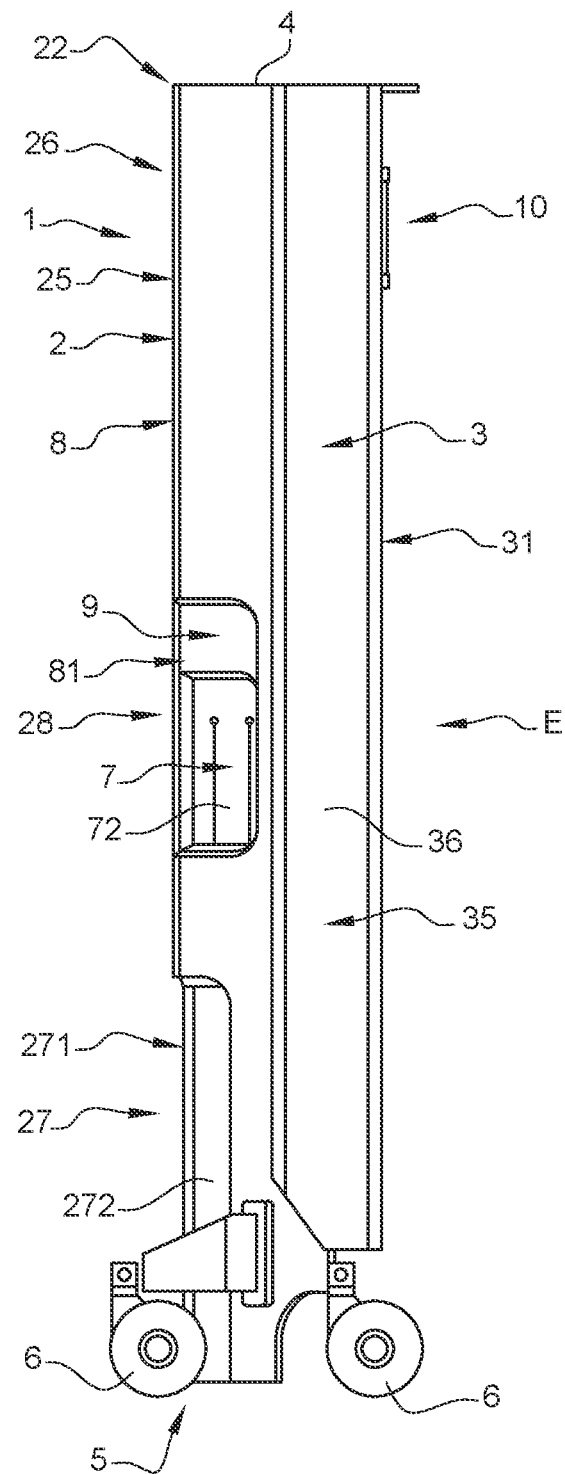
FIG. 3 is a side view of the radio-protective screen shown in FIGS. 1 and 2.
Figure 4:
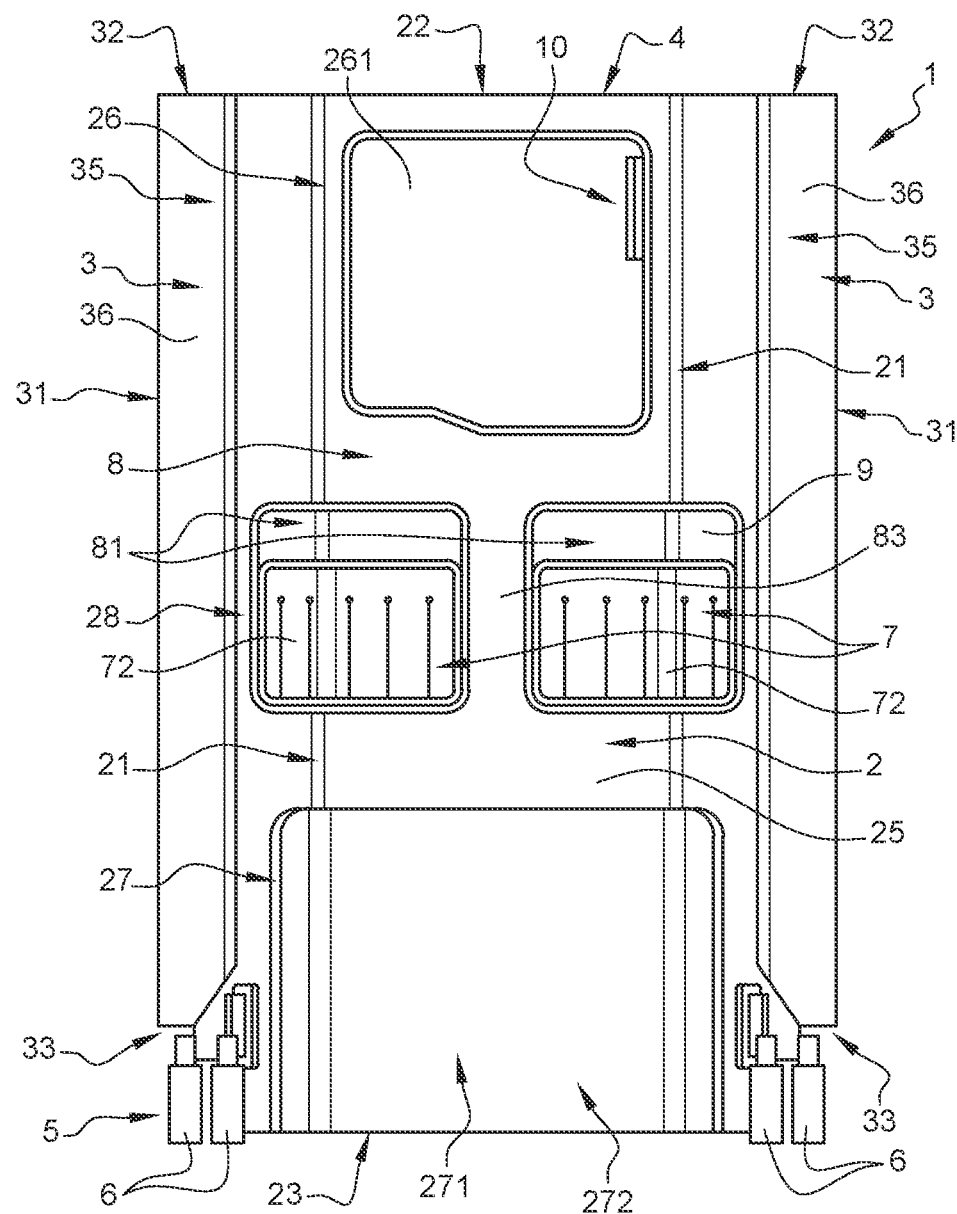
FIG. 4 is a front view of the exterior side (opposite the operator's positioning space) of the radio-protective screen shown in FIGS. 1 to 3.
Figure 5:
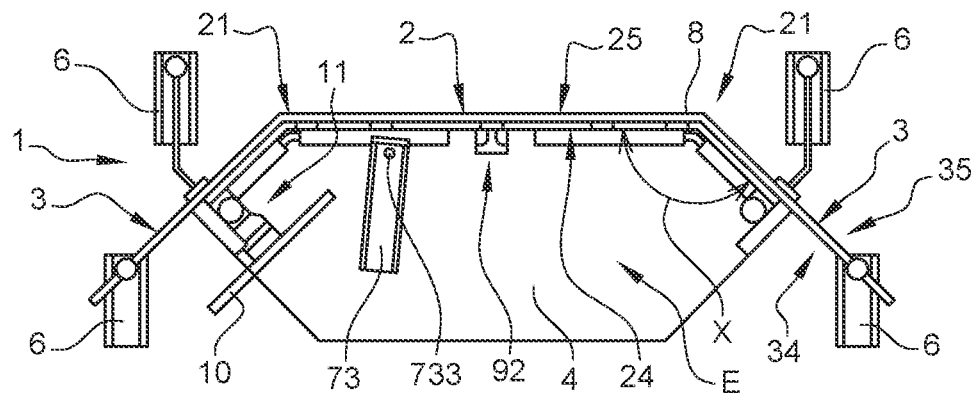
FIG. 5 is a top view of the radio-protective screen illustrated in FIGS. 1 to 4.

As can be seen in FIGS. 1, 2, and 4, in the illustrated embodiment, the outer panel opening 81 and the inner panel opening 91 comprise two opening parts juxtaposed horizontally and separated by a vertical upright, respectively 83 and 93.

These two vertical uprights 83 and 93 are arranged facing each other and they can be used as a support for the aforementioned weight compensator jack(s).

The flexible closing structure 72 equips the two parts of the interior panel opening 91, on each side of the vertical upright 93.

This flexible closing structure 72 is arranged to close the two parts of the interior panel opening 91 as effectively as possible, while allowing their separation to allow material and/or the operator's arms to pass.

The flexible closing structure 72 may consist of a juxtaposition of a plurality of vertical strips made of radio-protective material; this juxtaposition of vertical strips can be fixed at the upper part of each of the two parts of the interior panel opening 91 (for example by means of screwed fastening metal profiles), and it extends over the entire width and over the full height of both parts of the interior panel opening 91.

Such flexible strips can be obtained from a flexible panel made of Novashield (registered trademark), which consists of a flexible lead-free radio-protective material.

As a variant, the strips of flexible material can be replaced by strips formed from a juxtaposition of rigid links of radiation-protective material, connected to each other by joints.

As illustrated in the appended figures, the airlock structure 7 extends over the entire width of the front wall 2 and over part of the width of each side wall 3. Here, to this end, the interior panel 9 of the airlock structure 7 has a trihedral shape consisting of a juxtaposition of three faces angularly offset from each other. The rail structure 7111 which carries the support device 73 is formed along the lower opening edge 711 of the two parts of the interior panel opening 91. This rail structure 7111 is made up of several sections which follow the trihedral shape of the inner panel 9.

In an alternative embodiment, the front wall 2 can be provided with a single side wall 3; and yet in another alternative embodiment, this front wall 2 may not include a side wall. The general shape of the airlock structure 7 is then adapted accordingly.

According to another advantageous feature, the radio-protective screen 1 comprises a screen 10 arranged in the positioning space of the operator E.

This screen 10 is suitable for displaying useful information for the operator positioned in space E. For example, this screen 10 can display the biological parameters of the patient (heart rate, temperature, blood pressure, etc.), as well as the images obtained by the fluoroscopy system (C-Arm).

The screen 10 is mounted on a screen support 11 which is fixed on the inside face of front wall 24 or on an inside face of side wall 34.

In this case, in the illustrated embodiment, a screen support 11 is fixed to each of the side walls 3, on the side of the operator's positioning space E, to allow a choice of the most judicious positioning of screen 10.

For example, the radio-protective screen 1 according to the invention can be made from a metal sheet frame 12 mm thick, forming the outer panel 8 of the front wall 2 and part of the side walls 3, which metal frame includes:
an upper opening for positioning the transparent panel 261, added on the side of the operator positioning space E, and fixed by any appropriate means, for example plastic pins;
the outer panel opening 81, for positioning facing the movable inner panel 9 equipped with the support device 73;
the lower opening 271 for positioning the panel 272 made of flexible radio-protective material, attached to the side of the operator's positioning space E, and fixed by any appropriate means (for example by screwed metal fixing profiles at the upper edge of this lower opening 271);
the flexible flaps 36 made of radio-protective material attached and fixed by any appropriate means to the outer side edges 31 of the side walls 3;

the ceiling structure 4 formed of a transparent panel of radio-protective material, which extends horizontally from the upper edge 22 of the front wall 2, and from the upper edge 32 of the side walls 3, fixed by any appropriate means;

the base 5 provided with wheels 6 for ground support;

screen 10 with its screen support 11.

When used in the operating room, the radio-protective screen 1 is associated with equipment, in the form of a sterile cover, intended to cover at least part of its height.

Such an equipment in the form of a cover, shown schematically in FIG. 2, may include:

a flexible panel 12 adapted to at least partially cover the inner and outer faces of the front wall 2 and the side walls 3. This flexible panel 12 has an opening at its part intended to be positioned opposite the airlock structure 7; and it comprises a transparent part intended to be positioned opposite the transparent panel 261 of the upper part 26 of the front wall 2. The panel 12 further comprises fixing means to allow its fixing on the front wall 2 and/or on the side walls 3. These fastening means can for example consist of fasteners, adhesive strips or self-gripping strips;

at least one flexible airlock structure 13, adapted to at least partially cover the flexible closing structure 72 associated with the airlock opening 71 of the airlock structure 7. This flexible airlock structure 13 may be in the form of at least one flexible pocket provided with an opening, which flexible pocket is adapted to cover said flexible closing structure 72 by engagement of the lower edge of the latter in the opening of said flexible pocket. This flexible airlock structure 13 is further provided with means to allow it to be attached to the airlock structure 7 (for example fasteners, adhesive strips or self-gripping strips);

in this case, the flexible airlock structure 13 may comprise two flexible pockets each adapted to cover one of the two parts of the flexible closing structure 72, on either side of the upright 93;

a flexible support device pocket 14, for covering the support device 73, which flexible support device pocket 14 comprises a pocket opening for its positioning on said support device 73. This flexible support device pocket 14 is provided with means for its attachment to the support device 73 (for example fasteners, adhesive strips or self-gripping strips).

The invention claimed is:

1. Radiation protection screen for protecting an operator against the emission of ionizing radiation of an X-ray, which the screen comprises a front wall made at least in part from a radiation-protective material, which the front wall comprises a front wall inner face, facing an operator positioning space, a front wall outer face, opposite to said front wall inner face, an upper part, a lower part and an intermediate part located between said upper and lower parts, which the upper part comprises at least one transparent panel and which the intermediate part comprises an airlock structure, suitable for the passage of material and/or the arms of said operator, wherein said airlock structure comprises an airlock opening associated with a flexible closing structure, which the airlock opening comprises a lower opening edge, horizontal or approximately horizontal, and wherein said screen comprises a support device suitable for supporting material and/or an operator's arm, which support device is arranged at said lower edge opening, on the side of said inner face of the front wall.

2. The radiation protection screen according to claim 1, wherein said support device comprises a proximal end located close to said lower edge of the opening and an opposite distal end, and wherein said proximal end of said support device is pivotally mounted about a vertical or approximately vertical axis.

3. The radiation protection screen according to claim 2, further comprising adjustment means to allow adjustment of the position of said support device over at least part of the length of said lower opening edge.

4. The radiation protection screen according to claim 2, wherein said support device is in the form of an elongated body.

5. The radiation protection screen according to claim 2, wherein said front wall comprises an outer panel, forming at least part of said outer face of the front wall, which the outer panel comprises an outer panel opening located at the intermediate part of the front wall, and an inner panel, movable vertically, arranged facing said opening of outer panel, on the side of said inner face of front wall, which the inner panel comprises an inner panel opening, which the inner panel opening comprises said flexible closing structure and comprises said lower opening edge equipped with said support device, which the outer panel opening and the inner panel opening together form said airlock opening, and which the inner panel is movably mounted vertically relative to said outer panel so as to allow the height level of said airlock opening to be adjusted.

6. The radiation protection screen according to claim 1, further comprising adjustment means to allow adjustment of the position of said support device over at least part of the length of said lower opening edge.

7. The radiation protection screen according to claim 6, wherein said adjustment means consist of a rail structure formed along said lower edge of the opening, cooperating with a slider structure integral with said support device, which the slider structure is provided with locking means adapted to allow locking of its position on said rail structure.

8. The radiation protection screen according to claim 7, wherein said support device is in the form of an elongated body.

9. The radiation protection screen according to claim 6, wherein said support device is in the form of an elongated body.

10. The radiation protection screen according to claim 1, wherein said support device is in the form of an elongated body.

11. The radiation protection screen according to claim 10, wherein said support device is in the form of a chute with a U-section.

12. The radiation protection screen according to claim 1, wherein said front wall comprises an outer panel, forming at least part of said outer face of the front wall, which the outer panel comprises an outer panel opening located at the intermediate part of the front wall, and an inner panel, movable vertically, arranged facing said opening of outer panel, on the side of said inner face of front wall, which the inner panel comprises an inner panel opening, which the inner panel opening comprises said flexible closing structure and comprises said lower opening edge equipped with said support device, which the outer panel opening and the inner panel opening together form said airlock opening, and which the inner panel is movably mounted vertically relative to said outer panel so as to allow the height level of said airlock opening to be adjusted.

13. The radiation protection screen according to claim 12, wherein said inner panel is movably mounted along vertical rails located on said outer panel, in association with weight compensating means, which the inner panel is provided with an maneuvering handle and comprises an indexing finger cooperating with a plurality of indexing holes provided on said outer panel, to ensure the locking of its height position.

14. The radiation protection screen according to claim 12, wherein said inner panel opening and said outer panel opening each comprise two opening parts juxtaposed horizontally and separated by a vertical upright.

15. The radiation protection screen according to claim 1, wherein said flexible closing structure consists of a juxtaposition of a plurality of vertical strips made of radio-protective material.

16. The radiation protection screen according to claim 1, wherein said front wall extends in a vertical or approximately vertical plane and comprises two side edges, at least one of said two side edges of said front wall extending by a side wall which extends in a vertical or approximately vertical plane, at an angle of between 90° and 140° with respect to the plane of said front wall, seen from the side of said inner face of the front wall, which the side wall comprise an outer side edge fitted with a flexible flap made of radio-protective material.

17. The radiation protection screen according to claim 1, wherein said front wall extends in a vertical or approximately vertical plane and comprises two side edges each extending by a side wall, which the side walls each extend in a vertical or approximately vertical plane, at an angle comprised between 90° and 140° with respect to the plane of said front wall, seen from the side of said front wall inner face, and wherein said airlock structure extends over the entire width of said front wall and extends over part of the width of each of said side walls.

18. The radiation protection screen according to claim 1, further comprising a screen mounted on a screen support fixed to said inner face of the front wall on an inner face of one of its side walls.

19. The radiation protection screen according to claim 1, further comprising a base provided with ground support wheels, and wherein the lower part of the front wall and a lower part of the side walls comprise a panel of flexible radio-protective material.

20. Equipment in the form of a cover intended to cover at least part of the height of a radiation protection screen according to claim 1, comprising:

at least one flexible panel adapted to at least partially cover said front wall and if necessary at least partially said side wall, said at least one flexible panel comprising at least a transparent part intended to be positioned opposite the transparent panel of the upper part of said front wall, and fixing means on said front wall and/or on said side wall, at least one flexible airlock structure, adapted to at least partially cover the flexible closing structure associated with said airlock opening of said airlock structure, which the at least one flexible airlock structure is in the form of a flexible pocket provided with an opening, which the flexible pocket is adapted to cover said flexible closing structure by engagement of the lower edge of the flexible closing structure in said opening of said flexible pocket, which the flexible airlock structure is provided with means for its attachment to said airlock structure, and a flexible support device pocket, for covering said support device suitable for supporting material and/or an operator's arm, which the flexible support device pocket comprises a pocked opening for its positioning on said support device, which the flexible support device pocket is provided with means for its attachment to said support device.

\* \* \* \* \*